United States Patent
Sato et al.

(10) Patent No.: US 7,214,714 B2
(45) Date of Patent: May 8, 2007

(54) 20-HYDROXYEICOSATETRAENOIC ACID PRODUCTION INHIBITORS

(75) Inventors: Masakazu Sato, Toshima-ku (JP); Noriyuki Miyata, Toshima-ku (JP); Takaaki Ishii, Toshima-ku (JP); Yuko Matsunaga, Toshima-ku (JP); Hideaki Amada, Toshima-ku (JP)

(73) Assignee: Taisho Pharmaceutical Co. Ltd., Tokyo (JP)

( * ) Notice: Subject to any disclaimer, the term of this patent is extended or adjusted under 35 U.S.C. 154(b) by 299 days.

(21) Appl. No.: 10/475,869

(22) PCT Filed: Apr. 26, 2002

(86) PCT No.: PCT/JP02/04252

§ 371 (c)(1),
(2), (4) Date: Oct. 24, 2003

(87) PCT Pub. No.: WO02/088071

PCT Pub. Date: Nov. 7, 2002

(65) Prior Publication Data

US 2004/0121997 A1  Jun. 24, 2004

(30) Foreign Application Priority Data

Apr. 26, 2001  (JP) ............................. 2001-129794

(51) Int. Cl.
| | |
|---|---|
| A61K 31/136 | (2006.01) |
| A61K 31/402 | (2006.01) |
| C07C 259/14 | (2006.01) |
| C07D 207/20 | (2006.01) |
| C07D 211/00 | (2006.01) |
| C07D 213/00 | (2006.01) |
| C07D 215/00 | (2006.01) |
| C07D 241/00 | (2006.01) |
| C07D 295/00 | (2006.01) |
| C07D 491/00 | (2006.01) |

(52) U.S. Cl. ............... 514/609; 514/183; 514/217.12; 514/227.5; 514/235.5; 514/235.8; 514/238.2; 514/253.01; 514/253.13; 514/254.01; 514/255.01; 514/255.03; 514/278; 514/311; 514/315; 514/318; 514/326; 514/327; 514/330; 514/331; 514/357; 514/428; 540/481; 540/483; 540/609; 544/59; 544/121; 544/124; 544/166; 544/360; 544/372; 544/391; 544/392; 546/19; 546/164; 546/193; 546/216; 546/227; 546/231; 546/325; 546/332; 548/565; 564/229

(58) Field of Classification Search ............... 514/183, 514/217.12, 227.5, 235.5, 235.8, 238.2, 253.01, 514/253.13, 254.01, 255.01, 255.03, 278, 514/311, 315, 318, 326, 327, 330, 331, 357, 514/428, 609; 540/481, 483, 609; 544/59, 544/121, 124, 166, 360, 372, 391, 392; 546/19, 546/164, 193, 216, 227, 231, 325, 332; 548/565; 564/229

See application file for complete search history.

(56) References Cited

U.S. PATENT DOCUMENTS

| 5,356,921 A | 10/1994 | Ammann et al. ........... 514/397 |
| 6,864,254 B1 * | 3/2005 | Sato et al. ............... 514/238.8 |
| 2004/0110830 A1 * | 6/2004 | Sato et al. .................. 514/484 |

FOREIGN PATENT DOCUMENTS

| EP | 132 881 A1 | 2/1985 |
| JP | 2001-354656 A | 12/2001 |
| JP | 2001-354658 A | 12/2001 |
| WO | 99-43310 A2 | 9/1999 |
| WO | WO 01/32164 A1 | 5/2001 |
| WO | WO 01/96309 A1 | 12/2001 |

OTHER PUBLICATIONS

Alonso-Galicia, M. et al. "Inhibition of 20-HETE Production Contributes to the Vascular Responses to Nitric Oxide", Hypertension, vol. 29, No. 1, Jan. 1997, pp. 320-325.

* cited by examiner

Primary Examiner—Brenda Coleman
(74) Attorney, Agent, or Firm—Sughrue Mion, PLLC

(57) ABSTRACT

A hydroxyformamidine compound represented by the following formula or a pharmaceutically acceptable salt thereof

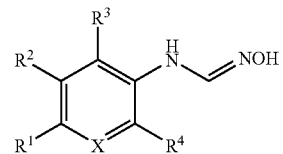

[wherein $R^1$ represents a substituted morpholino group, a substituted piperidino group, a piperazin-1-yl group, a substituted piperazin-1-yl group, a thiomorpholin-1-yl group, a perhydroazepin-1-yl group, a perhydroazocin-1-yl group, a tetrahydropyridin-1-yl group, a pyrrolin-1-yl group, etc.; X represents a nitrogen atom or a group represented by $CR^5$; and $R^2$ to $R^5$ are the same or different and each represents a hydrogen atom, a $C_{1-4}$ alkyl group, a $C_{1-4}$ alkoxy group, a trifluoromethyl group or a halogen atom.]

There is provided a drug which inhibits an enzyme producing 20-HETE participating in a contracting or dilating action for microvessels and an inducing action for cell proliferation in main organs such as kidney and cerebrovascular vessels.

2 Claims, No Drawings

20-HYDROXYEICOSATETRAENOIC ACID PRODUCTION INHIBITORS

This application is a 371 of PCT/JP02/04252, filed Apr. 26, 2002.

TECHNICAL FIELD

The present invention relates to hydroxyformamidinobenzene or hydroxyamidinopyridine derivatives which inhibit the production of 20-hydroxyeicosatetraenoic acid (20-HETE) from arachidonic acid.

BACKGROUND ART

With regard to physiologically active substances produced from arachidonic acid, there have been widely known prostaglandins produced by cyclooxygenase and leucotrienes produced by lipoxygenase while, in recent years, it has been becoming clear that 20-HETE produced from arachidonic acid by enzymes belonging to cytochrome p450 genus has varieties of actions in vivo (*J. Vascular Research*, volume 32, page 79 (1995)). Until now, it has been clarified that 20-HETE contracts or dilates the microvessels and also induces cell proliferation in main organs such as kidney and cerebrovascular vessels, and it has been suggested that 20-HETE deeply participates in pathology of various renal diseases, cerebrovascular diseases, circulatory diseases, etc. while playing an important physiological action in vivo (*J. Vascular Research*, volume 32, page 79 (1995); *Am. J. Physiol.*, volume 277, page R607 (1999); *Physiol. Rev.*, volume 82, page 131 (2002), etc.).

An object of the present invention is to provide a drug which inhibits the production of 20-HETE which participates in the contraction or dilation of microvessels, the induction of cell proliferation, etc. in main organs such as kidney and cerebrovascular vessels.

DISCLOSURE OF THE INVENTION

As a result of extensive searches and investigations for the purpose of solving the above-mentioned problem, the present inventors have found that several aromatic compounds inhibit the production of 20-HETE, whereupon the present invention has been achieved.

That is, the present invention relates to a hydroxyformamidine compound represented by the following formula or a pharmaceutically acceptable salt thereof.

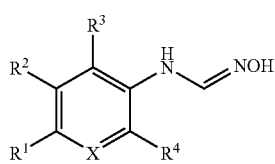
(1)

wherein $R^1$ represents a substituted morpholino group, a substituted piperidino group, a piperazin-1-yl group, a substituted piperazin-1-yl group, a thiomorpholin-1-yl group, a perhydroazepin-1-yl group, a perhydroazocin-1-yl group, a tetrahydropyridin-1-yl group, a pyrrolin-1-yl group, a 1,4-dioxa-8-azaspiro[4,5]decan-8-yl group, a decahydroquinolin-1-yl group, a mono or di ($C_{1-4}$ alkoxy $C_{1-6}$ alkyl)amino group, or a mono or di ($C_{1-6}$ hydroxyalkyl)amino group; X represents a nitrogen atom or a group represented by $CR^5$; and $R^2$ to $R^5$ are the same or different and each represents a hydrogen atom, a $C_{1-4}$ alkyl group, a $C_{1-4}$ alkoxy group, a trifluoromethyl group or a halogen atom.

The terms used in the present invention are defined as follows. The substituted morpholino group means a morpholino group which is substituted with 1 to 3 $C_{1-4}$ alkyl group(s) and its examples are 2-methylmorpholino group, 2-ethylmorpholino group, 3-methylmorpholino group, 2,6-dimethylmorpholino group and 2,3,5-trimethylmorpholino group where 2,6-dimethylmorpholino group is more preferred.

The substituted piperidino group means a piperidino group which is substituted with a $C_{1-4}$ alkyl group, a piperidino group which is substituted with a $C_{1-4}$ alkoxy group, a piperidino group which is substituted with a hydroxyl group, a piperidino group which is substituted with a $C_{2-5}$ alkoxycarbonyl group, a piperidino group which is substituted with a mono- or di-$C_{2-7}$ alkylaminocarbonyl group, a piperidino group which is substituted with a $C_{1-4}$ alkoxy-$C_{1-6}$ alkyl group, a piperidino group which is substituted with a $C_{1-6}$ hydroxyalkyl group and a piperidino group which is substituted with a mono- or di-$C_{1-4}$ alkylamino-$C_{1-6}$ alkyl group and its examples are 2-methylpiperidino group, 3-methylpiperidino group, 4-methylpiperidino group, 4-ethylpiperidino group, 4-methoxypiperidino group, 4-hydroxypiperidino group, 4-methoxycarbonylpiperidino group, 4-ethoxycarbonylpiperidino group, 4-dimethylaminocarbonylpiperidino group, 3-diethylaminocarbonylpiperidino group, 4 (2-methoxyethyl)piperidino group, 4-(2-hydroxyethyl)piperidino group and 4-(2-dimethylaminoethyl)piperidino group where 4-hydroxypiperidino group, 4-(2-hydroxyethyl)piperidino group, 4-ethoxycarbonylpiperidino group and 3-diethylaminocarbonylpiperidino group are more preferred.

The substituted piperazin-1-yl group means a piperazin-1-yl group, a piperazin-1-yl group which is substituted with a $C_{1-4}$alkyl group, a piperazin-1-yl group which is substituted with a cycloalkyl group having 4 to 8 ring members, a piperazin-1-yl group which is substituted with a $C_{1-4}$ alkoxy-$C_{1-4}$ alkyl group, a piperazin-1-yl group which is substituted with a $C_{1-6}$ hydroxyalkyl group, a piperazin-1-yl group which is substituted with a mono- or di-$C_{1-4}$ alkylamino-$C_{1-6}$ alkyl group, a piperazin-1-yl group which is substituted with a pyrrolidin-1-yl-$C_{1-6}$ alkyl group, a piperazin-1-yl group which is substituted with a morpholinocarbonyl-$C_{1-6}$ alkyl group, a piperazin-1-yl group which is substituted with a $C_{2-6}$ alkanoyl group, a piperazin-1-yl group which is substituted with a phenyl group and a piperazin-1-yl group which is substituted with a pyridyl group and its examples are 2-methylpiperazin-1-yl group, 3-methylpiperazin-1-yl group, 4-methylpiperazin-1-yl group, 4-ethylpiperazin-1-yl group, 4-cyclohexylpiperazin-1-yl group, 4-(2-methoxyethyl)piperazin-1-yl group, 4-(2-hydroxyethyl)piperazin-1-yl group, 4-(2-dimethylaminoethyl)piperazin-1-yl group, 4-(2-pyrrolidin-1-yl-ethyl)piperazin-1-yl group, 4-(1-morpholinocarbonylmethyl)piperazin-1-yl group and 4-phenylpiperazin-1-yl group where 4-methylpiperazin-1-yl group, 4-ethylpiperazin-1-yl group, 4-cyclohexylpiperazin-1-yl group, 4-(2-hydroxyethyl)piperazin-1-yl group, 4-(2-dimethylaminoethyl)piperazin-1-yl group, 4-(2-pyrrolidin-1-yl-ethyl)piperazin-1-yl group, 4-(morpholinocarbonylmethyl)piperazin-1-yl group, 4-acetylpiperazin-1-yl group, 4-phenylpiperazin-1-yl group and 4-(2-pyridyl)piperazin-1-yl group are more preferred.

In the present invention, "$C_{x-y}$" means that a group thereafter has x to y carbon atoms.

The halogen atom is fluorine atom, chlorine atom, bromine atom or iodine atom.

The $C_{1-4}$ and $C_{1-6}$ alkyl groups mean a linear or branched alkyl group having 1–4 and 1–6 carbon atom(s), respectively and examples of the $C_{1-4}$ alkyl group are methyl group, ethyl group, propyl group, isopropyl group, butyl group, isobutyl group and tert-butyl group where methyl group is more preferred. Example of the $C_{1-6}$ alkyl group are methyl group, ethyl group, propyl group, isopropyl group, butyl group, isobutyl group, tert-butyl group, pentyl group, isopentyl group, hexyl group and isohexyl group where methyl group and ethyl group are more preferred.

The $C_{1-4}$ alkoxy group means a linear or branched alkoxy group having 1 to 4 carbon(s) and its examples are methoxy group, ethoxy group, propoxy group, isopropoxy group, butoxy group and tert-butoxy group.

The $C_{2-5}$ alkoxycarbonyl group means a substituent in a compounded form of a linear or branched alkoxy group having 1 to 4 carbon(s) with carbonyl group and its examples are methoxycarbonyl group, ethoxycarbonyl group, propoxycarbonyl group, isopropoxycarbonyl group and butoxycarbonyl group.

The mono- or di-$C_{2-7}$ alkylaminocarbonyl group means a substituent in a compounded form of an amino group, which is substituted with one or two linear or branched alkyl group(s) having 1 to 6 carbon (s), with carbonyl group and its examples are methylaminocarbonyl group, ethylaminocarbonyl group, dimethylaminocarbonyl group, diethylaminocarbonyl group and diisobutylaminocarbonyl group where diethylaminocarbonyl group is more preferred.

The $C_{1-4}$ alkoxy-$C_{1-4}$ alkyl group means a substituent in a compounded form of a linear or branched alkoxy group having 1 to 4 carbon(s) with a linear or branched alkyl group having 1 to 4 carbon(s) and its examples are methoxymethyl group, ethoxymethyl group, methoxyethyl group, ethoxyethyl group, propoxyethyl group, isopropoxyethyl group, butoxyethyl group and tert-butoxyethyl group.

The $C_{1-6}$ hydroxyalkyl group means a linear or branched alkyl group having 1 to 6 carbon(s) substituted with hydroxyl group and its examples are hydroxymethyl group, 1-hydroxyethyl group, 2-hydroxyethyl group, 3-hydroxypropyl group and 5-hydroxypentyl group where the more preferred one is 2-hydroxyethyl group.

The mono- or di-$C_{1-4}$ alkylamino-$C_{1-6}$ alkyl group means a substituent in a compounded form of an amino group, which is substituted with one or two linear or branched alkyl group(s) having 1 to 4 carbon(s), with a linear or branched alkyl group having 1 to 6 carbon (s) and its examples are methylaminomethyl group, 1-methylaminoethyl group, 2-methylaminoethyl group, 3-methylaminopropyl group, 4-dimethylaminobutyl group, dimethylaminomethyl group, 1-dimethylaminoethyl group, 2-dimethylaminoethyl group and 3-dimethylaminopropyl group where 2-dimethylaminoethyl group is more preferred.

The cycloalkyl group having 4 to 8 ring members means cyclobutyl group, cyclopentyl group, cyclohexyl group, cycloheptyl group and cyclooctyl group where cyclohexyl group is more preferred.

The pyrrolidin-1-yl-$C_{1-6}$ alkyl group means a linear or branched alkyl group having 1 to 6 carbon(s) substituted with a pyrrolidin-1-yl group and its examples are pyrrolidin-1-yl-methyl group, 2-(pyrrolidin-1-yl)ethyl group, 3-(pyrrolidin-1-yl)propyl group and 5-(pyrrolidin-1-yl)pentyl group where 2-(pyrrolidin-1-yl)ethyl group is more preferred.

The morpholinocarbonyl-$C_{1-6}$ alkyl group is a linear or branched alkyl group having 1 to 6 carbon(s) substituted with a morpholinocarbonyl group and its examples are morpholinocarbonylmethyl group, 2-morpholinocarbonylethyl group, 3-morpholinocarbonylpropyl group and 5-morpholinocarbonylpentyl group where morpholinocarbonylmethyl group is more preferred.

Melting points, measured MASS values, Rf values of TLC and developing solvents of those compounds are shown in Table 1. In the TLC measurement, $SiO_2$ (NH) manufactured by Fuji Silysia Chemical Ltd. was used.

The pharmaceutically acceptable salt is a salt with alkaline metal, alkaline earth metal, ammonium, alkylammonium, etc. and a salt with mineral acid or organic acid. Its examples are sodium salt, potassium salt, calcium salt, ammonium salt, aluminum salt, triethylammonium salt, acetate, propionate, butyrate, formate, trifluoroacetate, maleate, tartrate, citrate, stearate, succinate, ethylsuccinate, lactobionate, gluconate, glucoheptonate, benzoate, methanesulfonate, ethanesulfonate, 2-hydroxyethanesulfonate, benzenesulfonate, p-toluenesulfonate, laurylsulfate, malate, aspartate, glutamate, adipate, a salt with cysteine, a salt with N-acetylcysteine, hydrochloride, hydrobromide, phosphate, sulfate, hydroiodide, nicotinate, oxalate, picrate, thiocyanate, undecanoate, a salt with acrylic acid polymer and a salt with carboxyvinyl polymer.

The compound of the present invention can, for example, be synthesized by the method shown below. That is, a compound represented by the following formula (a):

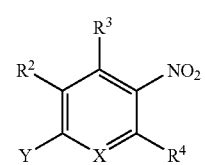

(a)

(wherein Y is a halogen atom, and $R^2$, $R^3$, $R^4$ and X have the same meanings as mentioned above) is made to react with a compound represented by the following formula (b):

$R^1H$           (b)

(wherein $R^1$ has the same meaning as mentioned above) in the presence or absence of a suitable solvent to give a compound represented by the following formula (c). (wherein $R^1$, $R^2$, $R^3$, $R^4$ and X have the same meanings as mentioned above.)

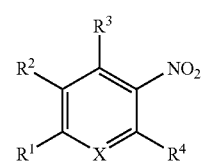

(c)

Then, a nitro group of the compound (c) is reduced using a reducing agent (such as palladium-activated carbon hydrogen in an atmosphere, palladium-activated carbon/hydrazine hydrate, palladium-activated carbon/ammonium formate, stannous (II) chloride monohydrate, iron/ammonium chloride and Raney nickel/hydrazine hydrate) in a suitable solvent (such as methanol, ethanol, propanol, tetrahydrofuran, dioxane, toluene, methylene chloride, chloroform, acetonitrile and ethyl acetate) to manufacture an aniline derivative (d). (wherein $R^1$, $R^2$, $R^3$, $R^4$ and X have the same meanings as mentioned above.)

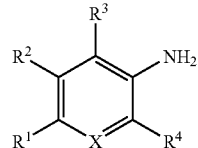

After that, the compound (d) is made to react with dimethylformamide dimethylacetal in a suitable solvent (such as methanol, ethanol, propanol, tetrahydrofuran, dioxane, toluene, methylene chloride, chloroform, acetonitrile and ethyl acetate) at from a room temperature to 150° C., preferably 70° C. to 100° C. for 2 to 72 hours. An intermediate which is prepared hereinabove is treated with hydroxylamine hydrochloride in a suitable solvent (such as methanol, ethanol, propanol, tetrahydrofuran, dioxane, toluene, methylene chloride, chloroform, acetonitrile and ethyl acetate) to manufacture the compound of the present invention represented by the formula (1). Alternatively, the compound of the formula (d) is made to react with an orthoformate such as trimethyl orthoformate or triethyl orthoformate in the presence or absence of a catalytic amount of an organic acid such as acetic acid, a mineral acid such as hydrochloric acid or a salt of amine with mineral acid such as pyridine hydrochloride to give an intermediate. The reaction temperature is from a room temperature to 150° C., preferably 70° C. to 100° C. and the reaction time is 2 to 72 hours. This is isolated or is not isolated and then treated with hydroxylamine in a suitable solvent (such as methanol, ethanol, propanol, tetrahydrofuran, dioxane, toluene, methylene chloride, chloroform, acetonitrile and ethyl acetate) to manufacture the compound of the present invention represented by the formula (1).

The medicine of the present invention contains the compound represented by the formula (1) as such or a pharmaceutically acceptable salt thereof as an effective ingredient. The medicine as such is useful particularly as a therapeutic agent for renal diseases, cerebrovascular diseases or circulatory diseases. The inhibitor for the production of 20-HETE according to the present invention contains the compound represented by the formula (1) or a pharmaceutically acceptable salt thereof as an effective ingredient and it effectively inhibits the production of 20-HETE.

The dosage of the medicine, the treating agent for renal diseases, cerebrovascular diseases and circulatory diseases, and the inhibitor for the production of 20-HETE according to the present invention is preferably 1 to 2,000 mg per day as the compound represented by the formula (1) or a pharmaceutically acceptable salt thereof in the case of treatment of adults and it can be administered once or by dividing into several time daily. The dosage can be appropriately increased or decreased depending upon the use and age, body weight, symptom, etc. of the patient.

The medicine, the treating agent for renal diseases, cerebrovascular diseases and circulatory diseases, and the inhibitor for the production of 20-HETE according to the present invention can be administered either orally or parenterally. The dosage forms thereof are tablets, capsules, granules, diluted powder, powder, troches, ointments, creams, emulsions, suspensions, suppositories, injections, etc. and all of them can be manufactured by the ordinary preparation method (for example, according to the methods stipulated by the 12th Revision of the Japanese Pharmacopoeia). Those dosage forms can be appropriately selected depending upon symptom, age and object of therapy of the patient. In the manufacture of the preparations of various dosage forms, it is possible to use ordinary used excipients (such as crystalline cellulose, starch, lactose and mannitol), binders (such as hydroxypropyl cellulose and polyvinylpyrrolidone), lubricants (such as magnesium stearate and talc), disintegrating agents (such as carboxymethyl cellulose calcium), etc.

BEST MODE FOR CARRYING OUT THE INVENTION

The present invention will now be illustrated in more detail by way of the following Examples.

EXAMPLE 1

Synthesis of N-hydroxyl-N'-(3-chloro-4-thiomorpholinophenyl)formamidine

A mixture of 3-chloro-4-fluoronitrobenzene (0.070 g, 0.4 mmol) and thiomorpholine (0.165 g, 1.6 mmol) was stirred at 70° C. for 16 hours. The reaction mixture was cooled down to room temperature, concentrated under a reduced pressure and purified by a silica gel column chromatography (developing solvents; chloroform:methanol=9:1) to obtain yellow powdery crystals. Iron powder (0.27 g, 4.83 mmol), isopropanol (0.5 ml) and 1 equivalent of aqueous solution of ammonium chloride (0.12 ml, 0.12 mol) were added thereto, followed by stirring at 70° C. for 16 hours. The reaction mixture was cooled down to room temperature, tetrahydrofuran (0.4 ml) was added thereto and insoluble matters were filtered off using Celite, followed by washing with ethyl acetate (0.4 ml) for four times. The filtrate was concentrated under a reduced pressure and methanol (0.4 ml) and dimethylformamide dimethylacetal (0.095 g, 0.8 mmol) were added thereto, followed by stirring at 70° C. for 64 hours. The reaction mixture was cooled down to room temperature and concentrated under a reduced pressure and methanol (0.4 ml) and hydroxylamine hydrochloride (0.033 g, 0.48 mmol) were added thereto, followed by stirring at room temperature for 6 hours. The reaction mixture was concentrated under a reduced pressure and a saturated aqueous solution of sodium hydrogen carbonate (0.4 ml) was added thereto, followed by extracting with ethyl acetate. The organic layer was concentrated under a reduced pressure, purified by an NH type silica gel column chromatography (developing solvents; n-hexane:ethyl acetate=1:1) and recrystallized from ethyl acetate/n-hexane to obtain the title compound (0.026 g) (the compound 3 in Table 1 which will be shown after) in colorless powder.

Melting point: 137.0 to 138.5° C.

EXAMPLE 2

Synthesis of N-[2-(morpholino)pyridine-5-yl]-N'-hydroxyformamidine

A mixture of 2-chloro-5-nitropyridine (2 g, 12.6 mmol) and morpholine (4.4 g, 50.5 mmol) was stirred at a room temperature for 1 hour. Water was added to the reaction mixture and the crystals separated out therefrom were filtered to obtain yellow powdery crystals. Methanol (30 ml) and palladium carbon (0.25 g) were added thereto, the mixture was stirred in a hydrogen atmosphere at a room temperature for 4 hours, insoluble matters were filtered off using Celite and the filtrate was concentrated under a reduced pressure. To the resulting residue were added methanol (20 ml) and dimethylformamide dimethylacetal (1.81 g, 15.2 mmol), followed by stirring under refluxing for 2 hours. The reaction mixture was cooled down to room temperature and concentrated under a reduced pressure, and methanol (20 ml) and hydroxylamine hydrochloride (1.05 g, 15.2 mol) were added thereto, followed by stirring at room temperature for 4 hours. The reaction mixture was concentrated under a reduced pressure and a saturated aqueous solution of sodium hydrogen carbonate (10 ml) was added thereto, followed by extracting with ethyl acetate. The organic layer was dried over $MgSO_4$, concentrated under a reduced pressure, purified by an NH type silica gel column chromatography (developing solvents; n-hexane:ethyl acetate=1:1) and recrystallized from ethyl acetate to obtain the title compound (0.985 g) (the compound 127 in Table 1 which will be shown after) in colorless powder.

Melting point: 172.0 to 174.0° C.

The compounds shown in the following table were synthesized by the same reaction operation as in Example 1 or 2 using the corresponding starting materials. The compounds obtained in Examples 1 and 2 are also shown therein as compounds 3 and 127.

| Comp. No. | Structural Formula | m.p. | M + H (APCI) | M − H (APCI) | Rf Value* | Developing Solvent | $IC_{50}$ (nM) |
|---|---|---|---|---|---|---|---|
| 1 | | 138.0–141.0 | | 236 | 0.23 | AcOEt | |
| 2 | | 141.0–142.0 (dec.) | | 254 | 0.25 | AcOEt | 3.2 |
| 3 | | 137.0–138.5 | 272 | 270 | 0.26 | AcOEt | 3.6 |
| 4 | | 149.0–151.0 | | 314 | 0.27 | AcOEt | 2.3 |

-continued

| Comp. No. | Structural Formula | m.p. | M + H (APCl) | M − H (APCl) | Rf Value* | Developing Solvent | IC$_{50}$ (nM) |
|---|---|---|---|---|---|---|---|
| 5 | thiomorpholine-phenyl(CF$_3$)-NH-CH=N-OH | | | 304 | 0.31 | AcOEt | |
| 6 | thiomorpholine-phenyl(CH$_3$)-NH-CH=N-OH | | | 252 | 0.29 | AcOEt | |
| 7 | 2,6-dimethylmorpholine-phenyl-NH-CH=N-OH | | | 248 | 0.23 | AcOEt | |
| 8 | 2,6-dimethylmorpholine-phenyl(F)-NH-CH=N-OH | | | 266 | 0.26 | AcOEt | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 9 | | 163.0–164.0 (dec.) | | 282 | 0.26 | AcOEt | 46.9 |
| 10 | | | | 316 | 0.31 | AcOEt | |
| 11 | | 118.0–121.0 | | 236 | 0.26 | AcOEt | 12.5 |
| 12 | | | | 280 | 0.27 | AcOEt | 16.0 |
| 13 | | | | 270 | 0.31 | AcOEt | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 14 | (4-(3,6-dihydro-2H-pyridin-1-yl)phenyl)aminomethylene hydroxylamine | | | 218 | 0.24 | AcOEt | |
| 15 | (4-(3,6-dihydro-2H-pyridin-1-yl)-3-fluorophenyl)aminomethylene hydroxylamine | 129.0–130.0 | | 234 | 0.26 | AcOEt | 3.9 |
| 16 | (4-(3,6-dihydro-2H-pyridin-1-yl)-3-chlorophenyl)aminomethylene hydroxylamine | 135.0–137.5 | | 250 | 0.26 | AcOEt | 2.2 |
| 17 | (4-(3,6-dihydro-2H-pyridin-1-yl)-3-bromophenyl)aminomethylene hydroxylamine | | | 294 | 0.27 | AcOEt | |
| 18 | (4-(3,6-dihydro-2H-pyridin-1-yl)-3-methylphenyl)aminomethylene hydroxylamine | | | 230 | 0.14 | AcOEt | |

-continued
| Comp. No. | Structural Formula | m.p. | M + H (APCI) | M − H (APCI) | Rf Value* | Developing Solvent | IC$_{50}$ (nM) |
|---|---|---|---|---|---|---|---|
| 19 | 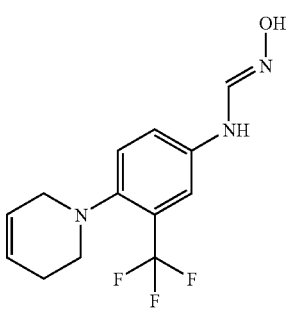 | 136.5–138.0 | | 284 | 0.33 | AcOEt | 18.0 |
| 20 | 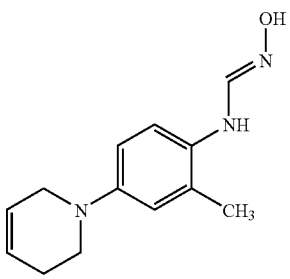 | 146.0–149.0 | | 230 | 0.29 | AcOEt | 663.0 |
| 21 | 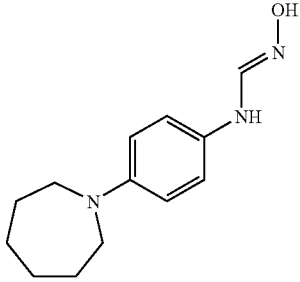 | | | 232 | 0.26 | AcOEt | |
| 22 | 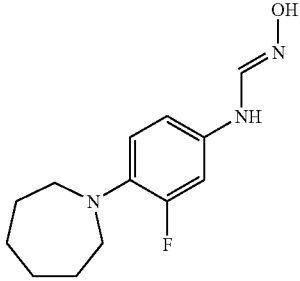 | 112.0–115.0 | | 250 | 0.30 | AcOEt | 2.1 |
| 23 | 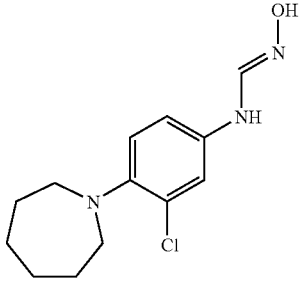 | 113.0–114.0 | | 266 | 0.29 | AcOEt | 2.2 |

-continued

| Comp. No. | Structural Formula | m.p. | M + H (APCl) | M − H (APCl) | Rf Value* | Developing Solvent | IC$_{50}$ (nM) |
|---|---|---|---|---|---|---|---|
| 24 | | 103.5–105.0 | | 310 | 0.30 | AcOEt | 4.2 |
| 25 | | | 248 | 246 | 0.31 | AcOEt | |
| 26 | | 127.0–128.5 | 302 | 300 | 0.29 | AcOEt | 25.2 |
| 27 | | 170.0–173.0 | 248 | 246 | 0.36 | AcOEt | 10.2 |
| 28 | | 137.0–139.0 | 266 | 264 | 0.38 | AcOEt | 5.7 |

-continued
| Comp. No. | Structural Formula | m.p. | M + H (APCI) | M − H (APCI) | Rf Value* | Developing Solvent | IC$_{50}$ (nM) |
|---|---|---|---|---|---|---|---|
| 29 | 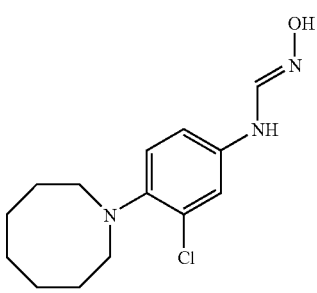 | | 282 | 280 | 0.38 | AcOEt | |
| 30 | 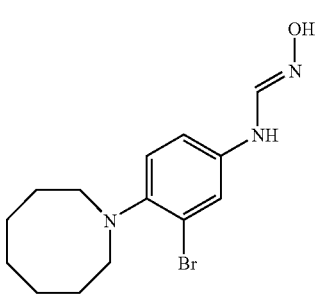 | | 326 | 324 | 0.34 | AcOEt | |
| 31 | 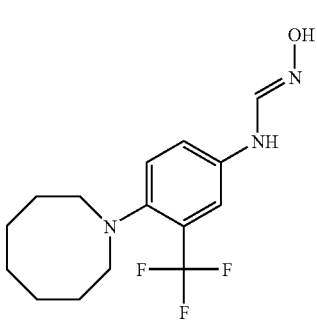 | | 316 | 314 | 0.39 | AcOEt | |
| 32 | 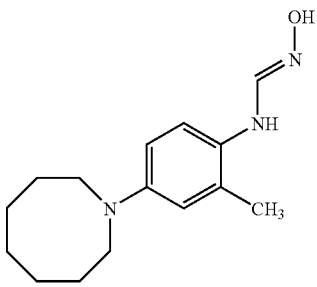 | | 262 | 360 | 0.38 | AcOEt | |
| 33 | 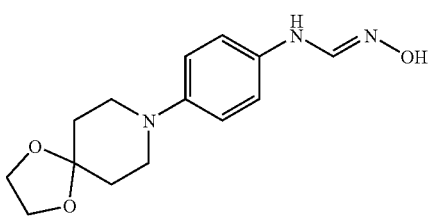 | 157.0–158.5 | 278 | 276 | 0.27 | AcOEt | 3.6 |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 34 | | 165.0–167.0 | 296 | 294 | 0.32 | AcOEt | 7.0 |
| 35 | | 174.0–176.0 | 312 | 310 | 0.32 | AcOEt | 5.0 |
| 36 | | 161.0–165.0 | | 355 | 0.32 | AcOEt | 3.3 |
| 37 | | | 292 | 290 | 0.30 | AcOEt | |
| 38 | | | 346 | 344 | 0.34 | AcOEt | |
| 39 | | 147.0–150.0 | 292 | 290 | 0.32 | AcOEt | 4.3 |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 40 | | | 274 | 272 | 0.32 | AcOEt | |
| 41 | | | 292 | 290 | 0.36 | AcOEt | |
| 42 | | | 308 | 306 | 0.34 | AcOEt | |
| 43 | | | 352 | 350 | 0.34 | AcOEt | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 44 | | | 288 | 286 | 0.36 | AcOEt | |
| 45 | | | 342 | 340 | 0.39 | AcOEt | |
| 46 | | 154.0–156.0 | 288 | 286 | 0.34 | AcOEt | 33 |
| 47 | | | | 234 | 0.11 | AcOEt | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 48 | (4-hydroxypiperidin-1-yl, 3-F phenyl, NH-CH=N-OH) | 159.0–161.0 | 254 | 252 | 0.16 | AcOEt | 3.2 |
| 49 | (4-hydroxypiperidin-1-yl, 3-Cl phenyl, NH-CH=N-OH) | 93.0–97.0 | 270 | 268 | 0.14 | AcOEt | 3.4 |
| 50 | (4-hydroxypiperidin-1-yl, 3-Br phenyl, NH-CH=N-OH) | | 314 | 312 | 0.16 | AcOEt | |
| 51 | (4-hydroxypiperidin-1-yl, 3-CH$_3$ phenyl, NH-CH=N-OH) | | 250 | 248 | 0.14 | AcOEt | |
| 52 | (4-hydroxypiperidin-1-yl, 3-CF$_3$ phenyl, NH-CH=N-OH) | | 304 | 302 | 0.18 | AcOEt | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 53 | | | | 248 | 0.13 | AcOEt | |
| 54 | | 186.0–189.0 | | 262 | 0.05 | AcOEt | 34.7 |
| 55 | | 172.0–176.0 | | 280 | 0.05 | AcOEt | 34.2 |
| 56 | | 179.0–181.0 | 343 | 341 | 0.16 | AcOEt | |
| 57 | | | 278 | 276 | 0.05 | AcOEt | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 58 | | 152.0–154.0 | 278 | 276 | 0.07 | AcOEt | 31.2 |
| 59 | | | 341 | 317 | 0.14 | AcOEt | |
| 60 | | | 359 | 335 | 0.18 | AcOEt | |
| 61 | | | 375 | 351 | 0.16 | AcOEt | |
| 62 | | | 397 | 395 | 0.16 | AcOEt | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 63 | | | 333 | 331 | 0.16 | AcOEt | |
| 64 | | 150–156.0 | 387 | 385 | 0.18 | AcOEt | 19.4 |
| 65 | | | 333 | 331 | 0.20 | AcOEt | |
| 66 | | | 235 | | 0.09 | AcOEt | |
| 67 | | | 253 | 251 | 0.12 | AcOEt | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 68 | | 188.0–189.0 | 269 | 267 | 0.11 | AcOEt | 106.6 |
| 69 | | | 249 | 247 | 0.19 | AcOEt | |
| 70 | | | | 301 | 0.14 | AcOEt | |
| 71 | | | 249 | 247 | 0.14 | AcOEt | |
| 72 | | 220.0–222.0 | | 247 | 0.11 | AcOEt | 39.2 |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 73 | (4-ethylpiperazinyl, 3-F phenyl oxime) | 197.0–200.0 | 267 | 265 | 0.14 | AcOEt | 37.2 |
| 74 | (4-ethylpiperazinyl, 3-Cl phenyl oxime) | 207.0–209.0 | 283 | 281 | 0.13 | AcOEt | 73.2 |
| 75 | (4-ethylpiperazinyl, 3-Br phenyl oxime) | 204.5–206.5 | 327 | 325 | 0.12 | AcOEt | 153.6 |
| 76 | (4-ethylpiperazinyl, 3-CH$_3$ phenyl oxime) | 161.0–165.0 | | 263 | 0.16 | AcOEt | 186.5 |
| 77 | (4-ethylpiperazinyl, 3-CF$_3$ phenyl oxime) | 158.0–159.0 | 317 | 315 | 0.16 | AcOEt | 509.0 |

| Comp. No. | Structural Formula | m.p. | M + H (APCl) | M − H (APCl) | Rf Value* | Developing Solvent | IC$_{50}$ (nM) |
|---|---|---|---|---|---|---|---|
| 78 | | | 263 | | 0.16 | AcOEt | |
| 79 | | 170.0 (dec.) | 265 | | 0.43 | CHCl$_3$; MeOH = 10:1 | 71.9 |
| 80 | | 180.0–182.0 (dec.) | 283 | 281 | 0.39 | CHCl$_3$; MeOH = 10:1 | 45.4 |
| 81 | | 200.0–202.0 (dec.) | 299 | | 0.38 | CHCl$_3$; MeOH = 10:1 | 23.3 |
| 82 | | 190.0–192.0 (dec.) | 343 | | 0.38 | CHCl$_3$; MeOH = 10:1 | 44.0 |

-continued
| Comp. No. | Structural Formula | m.p. | M + H (APCI) | M − H (APCI) | Rf Value* | Developing Solvent | IC$_{50}$ (nM) |
|---|---|---|---|---|---|---|---|
| 83 | 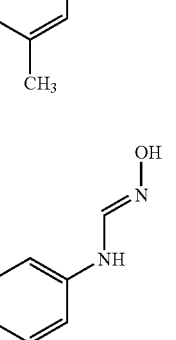 | | 279 | | 0.41 | CHCl$_3$; MeOH = 10:1 | |
| 84 | 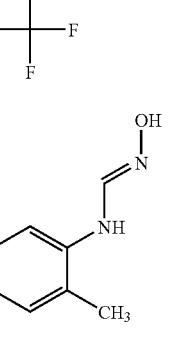 | | 333 | 331 | 0.34 | CHCl$_3$; MeOH = 10:1 | |
| 85 | 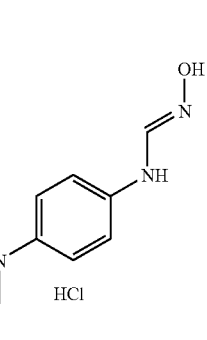 | | 279 | 277 | 0.46 | CHCl$_3$; MeOH = 10:1 | |
| 86 | 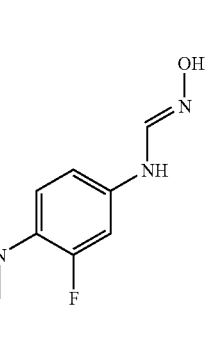 | 188.0–190.0 (dec.) | 292 | | 0.46 | CHCl$_3$; MeOH = 10:1 | 962.5 |
| 87 |  | | 310 | | 0.43 | CHCl$_3$; MeOH = 10:1 | |

-continued
| Comp. No. | Structural Formula | m.p. | M + H (APCI) | M − H (APCI) | Rf Value* | Developing Solvent | IC$_{50}$ (nM) |
|---|---|---|---|---|---|---|---|
| 88 | 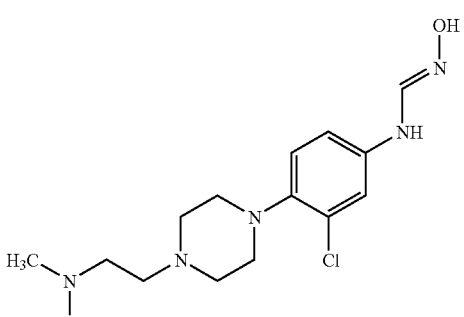 | | 326 | 324 | 0.44 | CHCl$_3$; MeOH = 10:1 | |
| 89 | 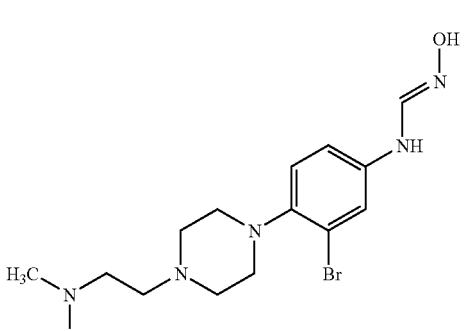 | | 373 | | 0.44 | CHCl$_3$; MeOH = 10:1 | |
| 90 | 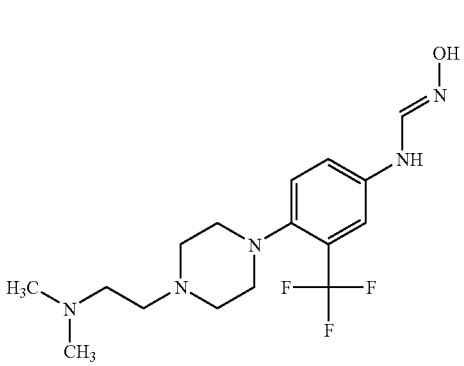 | | 360 | 358 | 0.41 | CHCl$_3$; MeOH = 10:1 | |
| 91 | 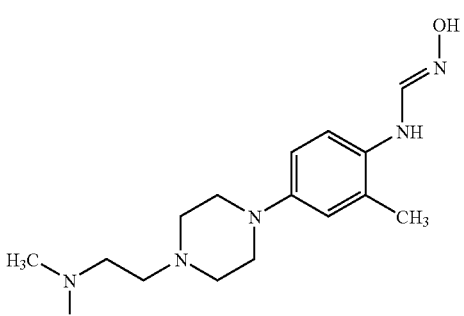 | | 306 | | 0.52 | CHCl$_3$; MeOH = 10:1 | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 92 | | | 318 | | 0.51 | CHCl$_3$; MeOH = 10:1 | |
| 93 | HCl | 205.0 (dec.) | 336 | 364 | 0.46 | CHCl$_3$; MeOH = 10:1 | 135.4 |
| 94 | HCl | 161.0–163.0 | 352 | | 0.46 | CHCl$_3$; MeOH = 10:1 | 222.4 |
| 95 | | 163.0–165.0 | 396 | | 0.46 | CHCl$_3$; MeOH = 10:1 | 75.8 |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 96 | | 229.0–231.0 (dec.) | 386 | 384 | 0.43 | CHCl$_3$; MeOH = 10:1 | 1534 |
| 97 | | 196.0–198.0 (dec.) | 332 | 330 | 0.51 | CHCl$_3$; MeOH = 10:1 | 758.1 |
| 98 | | 167.0–169.0 (dec.) | 348 | | 0.46 | CHCl$_3$; MeOH = 10:1 | 69.0 |
| 99 | | | 366 | | 0.44 | CHCl$_3$; MeOH = 10:1 | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 100 | (morpholine-C(O)-CH$_2$-piperazine-N-phenyl(Cl)-NH-CH=N-OH) · HCl | 110.0–114.0 | 382 | | 0.46 | CHCl$_3$; MeOH = 10:1 | 36.3 |
| 101 | (morpholine-C(O)-CH$_2$-piperazine-N-phenyl(Br)-NH-CH=N-OH) | | 426 | | 0.46 | CHCl$_3$; MeOH = 10:1 | 20.8 |
| 102 | (morpholine-C(O)-CH$_2$-piperazine-N-phenyl(CH$_3$)-NH-CH=N-OH) | | 362 | | 0.49 | CHCl$_3$; MeOH = 10:1 | |
| 103 | (morpholine-C(O)-CH$_2$-piperazine-N-phenyl(CF$_3$)-NH-CH=N-OH) | 75.0–77.0 | 416 | 414 | 0.46 | CHCl$_3$; MeOH = 10:1 | 21.4 |

-continued

| Comp. No. | Structural Formula | m.p. | M + H (APCl) | M − H (APCl) | Rf Value* | Developing Solvent | IC$_{50}$ (nM) |
|---|---|---|---|---|---|---|---|
| 104 | (morpholine-C(O)-CH$_2$-piperazine-phenyl(CH$_3$)-NH-CH=N-OH) | | 362 | 360 | 0.57 | CHCl$_3$; MeOH = 10:1 | |
| 105 | (cyclohexyl-piperazine-phenyl-NH-CH=N-OH) · HCl | 226.0–223.0 (dec.) | 303 | | 0.48 | CHCl$_3$; MeOH = 10:1 | 14.8 |
| 106 | (cyclohexyl-piperazine-phenyl(F)-NH-CH=N-OH) · HCl | 207.0 (dec.) | 321 | | 0.44 | CHCl$_3$; MeOH = 10:1 | 105.4 |
| 107 | (cyclohexyl-piperazine-phenyl(Cl)-NH-CH=N-OH) | | 337 | | 0.44 | CHCl$_3$; MeOH = 10:1 | 41.9 |
| 108 | (cyclohexyl-piperazine-phenyl(Br)-NH-CH=N-OH) · HCl | 222.0–223.0 (dec.) | 381 | | 0.44 | CHCl$_3$; MeOH = 10:1 | 293.0 |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 109 | | | 317 | | 0.49 | CHCl$_3$; MeOH = 10:1 | |
| 110 | | 93.0–96.0 | 371 | 369 | 0.44 | CHCl$_3$; MeOH = 10:1 | 531.2 |
| 111 | HCl | 230.0–232.0 (dec.) | 317 | | 0.56 | CHCl$_3$; MeOH = 10:1 | 70.8 |
| 112 | | | 297 | | 0.48 | CHCl$_3$; MeOH = 10:1 | |
| 113 | | | 315 | 297 | 0.46 | CHCl$_3$; MeOH = 10:1 | |

-continued

| Comp. No. | Structural Formula | m.p. | M + H (APCI) | M − H (APCI) | Rf Value* | Developing Solvent | IC$_{50}$ (nM) |
|---|---|---|---|---|---|---|---|
| 114 | | | 331 | 329 | 0.46 | CHCl$_3$; MeOH = 10:1 | |
| 115 | | | 375 | 373 | 0.46 | CHCl$_3$; MeOH = 10:1 | |
| 116 | | | 365 | 363 | 0.46 | CHCl$_3$; MeOH = 10:1 | |
| 117 | | | 311 | | 0.61 | CHCl$_3$; MeOH = 10:1 | |

| Comp. No. | Structural Formula | m.p. | M + H (APCI) | M − H (APCI) | Rf Value* | Developing Solvent | IC$_{50}$ (nM) |
|---|---|---|---|---|---|---|---|
| 118 | | | | 284 | 0.27 | AcOEt | |
| 119 | | 95.0–96.5 | | 300 | 0.26 | AcOEt | |
| 120 | | | | 334 | 0.29 | AcOEt | |
| 121 | | | | 266 | 0.33 | CHCl$_3$; MeOH = 10:1 | |

| Comp. No. | Structural Formula | m.p. | M + H (APCl) | M − H (APCl) | Rf Value* | Developing Solvent | IC$_{50}$ (nM) |
|---|---|---|---|---|---|---|---|
| 122 | | | 349 | | 0.44 | CHCl$_3$; MeOH = 10:1 | |
| 123 | HCl | 224.0–226.0 (dec.) | 304 | | 0.43 | CHCl$_3$; MeOH = 10:1 | 90.6 |
| 124 | | | 249 | 247 | 0.38 | AcOEt | |
| 125 | | | 279 | 277 | 0.23 | AcOEt | |
| 126 | | | 237 | 235 | 0.31 | AcOEt | |

-continued

| Comp. No. | Structural Formula | m.p. | M + H (APCl) | M − H (APCl) | Rf Value* | Developing Solvent | IC$_{50}$ (nM) |
|---|---|---|---|---|---|---|---|
| 127 | | 172.0–174.0 | | 221 | 0.22 | AcOEt | 215.4 |
| 128 | | 172.0–174.0 | | | | | 215.4 |
| 129 | | 191.0–192.0 (dec.) | | | | | 8.3 |
| 130 | | 189.0–190.0 (dec.) | | | | | 46.1 |
| 131 | | 94.0–96.0 | | | | | 3.5 |
| 132 | | 151.0–153.0 | | | | | 37.3 |

-continued

| Comp. No. | Structural Formula | m.p. | M + H (APCl) | M − H (APCl) | Rf Value* | Developing Solvent | IC$_{50}$ (nM) |
|---|---|---|---|---|---|---|---|
| 133 | 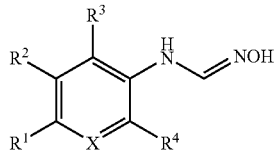 | 97.0–98.0 | | | | | 340.5 |
| 134 | 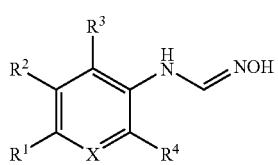 | 135.0–138.0 (dec.) | | | | | 4.0 |

*TLC Plate NH Fuji Silysia Chemical LTD.

TEST EXAMPLE

Inhibitory Action to 20-HETE-Producing Enzyme derived from Human Renal Microsome With regard to the compounds listed in the above table, their inhibitory actions to 20-HETE production were tested.

This test was carried out in accordance with a method mentioned in *J. Pharmacol. Exp. Ther.*, volume 268, page 474 (1994).

A solution of the test compound adjusted to 1 μM using DMSO was added to a 50 mM of 3-morpholinopropane-sulfonic acid buffer (MOPS) (pH 7.4) containing 5 mM of magnesium chloride and 1 mM of sodium ethylenediamine-tetraacetate (EDTA), then human renal microsome fraction (Human Cell Culture Center, Anatomic Gift Foundation), [5,6,8,9,11,12,15]tritium-arachidonic acid and NADPH were added thereto as an enzymatic source, a substrate and a coenzyme, respectively and reaction was carried out at 37° C. for 1.5 hours. Formic acid was added to the reaction solution to stop the reaction and then acetonitrile was added thereto (final concentration: 50%). Amount of 20-HETE produced thereby was measured using a high performance liquid chromatography equipped with a radioactive substance detector having an ODS column (Biosil C18; manufactured by Biorad).

Amount of 20-HETE produced when no compound was added was defined as 100% and the concentration of the compound when production of 20-HETE was inhibited to an extent of 50% upon addition of a compound (IC$_{50}$ value) was calculated. The results are also shown in the above table.

INDUSTRIAL APPLICABILITY

The compound represented by the formula (1) or a pharmaceutically acceptable salt thereof is useful as an inhibitor for the production of 20-HETE. It is also useful as a medicine, particularly as an agent for the treatment of renal diseases, cerebrovascular diseases and circulatory diseases.

What is claimed is:

1. A hydroxyformamidine compound represented by the following formula or a pharmaceutically acceptable salt thereof:

wherein $R^1$ represents a substituted piperidino group, a piperazin-1-yl group, a substituted piperazin-1-yl group, a thiomorpholin-1-yl group, a perhydroazepin-1-yl group, a perhydroazocin-1-yl group, a tetrahydropyridin-1-yl group, a pyrrolin-1-yl group, a 1,4-dioxa-8-azaspiro[4,5]decan-8-yl group, or a decahydroquinolin-1-yl group; X is a nitrogen atom or a group represented by $CR^5$; and $R^2$ to $R^5$ are the same or different and each represents a hydrogen atom, a $C_{1-4}$ alkyl group, a $C_{1-4}$ alkoxy group, a trifluoromethyl group or a halogen atom.

2. A method for treatment of renal diseases, cerebrovascular diseases and circulatory diseases, said method comprising administering to a subject in need of treatment an effective amount of the hydroxyformamidine compound represented by the following formula or a pharmaceutically acceptable salt thereof as an effective ingredient:

wherein $R^1$ represents a substituted piperidino group, a piperazin-1-yl group, a substituted piperazin-1-yl group, a thiomorpholin-1-yl group, a perhydroazepin- 1-yl group, a perhydroazocin-1-yl group, a tetrahydropyridin-1-yl group, a pyrrolin-1-yl group, a 1,4-dioxa-8-azaspiro[4,5]decan-8-yl group, a decahydroquinolin-1-yl group, a mono- or di-($C_{1-4}$ alkoxy-$C_{1-6}$ alkyl) amino group, or a mono or di-($C_{1-6}$ hydroxyalkyl) amino group; X is a nitrogen atom or a group represented by $CR^5$; and $R^2$ to $R^5$ are the same or different and each represents a hydrogen atom, a $C_{1-4}$ alkyl group, a $C_{1-4}$ alkoxy group, a trifluoromethyl group or a halogen atom.

* * * * *